United States Patent [19]

Okada

[11] 4,117,987
[45] Oct. 3, 1978

[54] FILM CASSETTE FOR AN ENDOSCOPE

[75] Inventor: Takeshi Okada, Hachioji, Japan

[73] Assignee: Olympus Optical Co., Ltd., Tokyo, Japan

[21] Appl. No.: 797,689

[22] Filed: May 17, 1977

Related U.S. Application Data

[62] Division of Ser. No. 703,606, Jul. 8, 1976, Pat. No. 4,038,977.

[30] Foreign Application Priority Data

Jul. 11, 1975 [JP] Japan .................................. 50-85077

[51] Int. Cl.² ......................... G03B 1/04; G03B 15/14; A61B 1/06
[52] U.S. Cl. ....................................... 242/71.2; 128/6; 242/67.3 R
[58] Field of Search ....................... 242/71.1, 71, 71.2, 242/71.7, 67.1 R, 67.3 R, 55, 71.3, 71.4, 71.5, 71.6, 179, 199; 354/62, 63, 212, 213, 214, 275; 128/4, 5, 6, 7, 8; 46/117, 118; 33/314; 352/72, 78 R

[56] References Cited

U.S. PATENT DOCUMENTS

| 2,206,381 | 7/1940 | Zimmerman | 242/71.2 |
| 2,641,977 | 6/1953 | Usi et al. | 354/62 |
| 3,426,663 | 2/1969 | Fox | 128/6 |
| 3,528,627 | 9/1970 | Sindlinger | 242/201 |

Primary Examiner—George F. Mautz

[57] ABSTRACT

An endoscope has within the forward end section of a sheath a cassette loaded with a roll of film on which a body cavity of a human being is photographed. One end of a film take-up shaft on the cassette outwardly extends from a housing of the cassette and a pulley is fixed on the outer periphery of the extending end portion of the film take-up shaft. A string is wound around the pulley. The string is inserted through a single passage in the sheath and when the string is pulled by an operator at a control section the film is wound.

2 Claims, 8 Drawing Figures

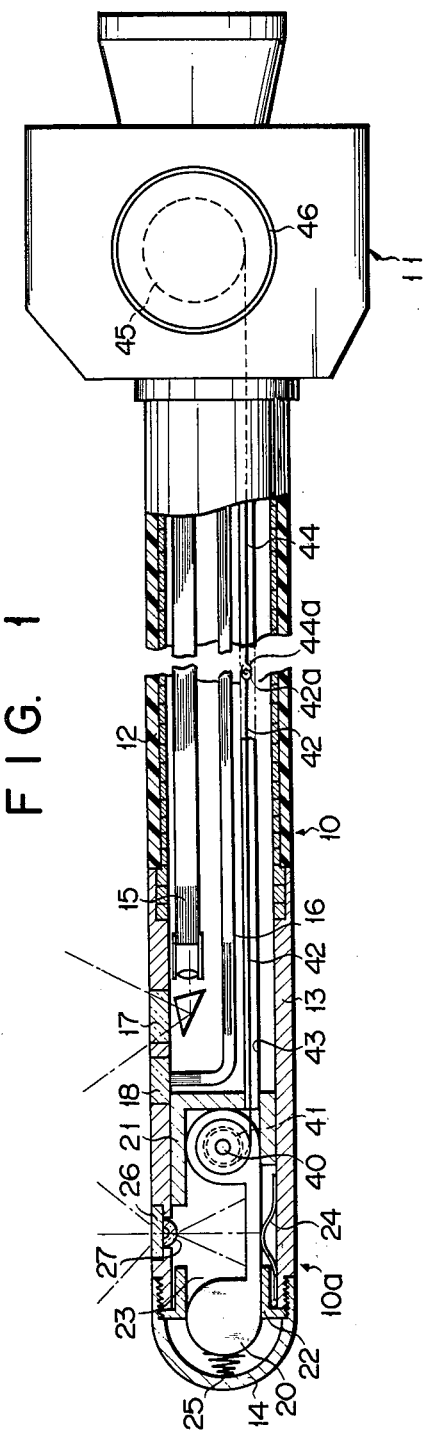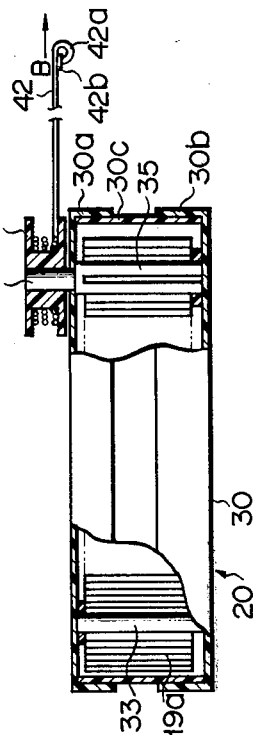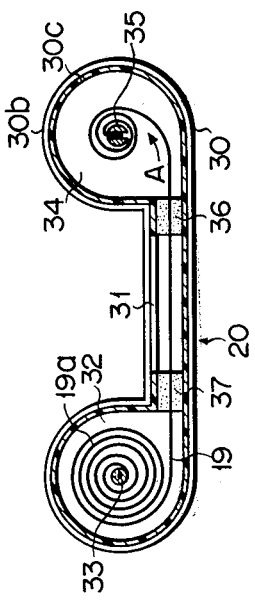

FIG. 6
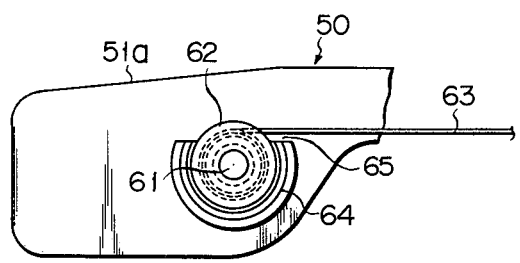
FIG. 7
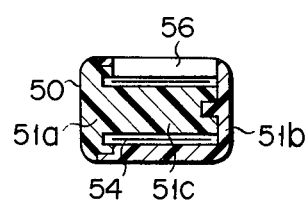
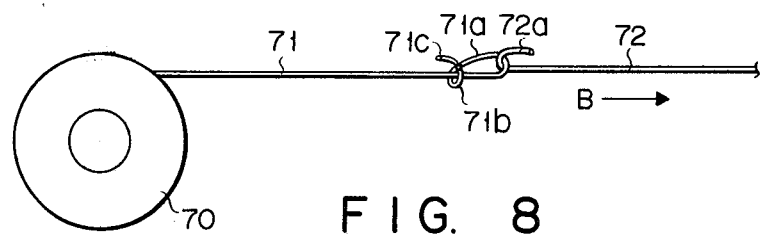
FIG. 8

FILM CASSETTE FOR AN ENDOSCOPE

This is a division of application Ser. No. 703,606, filed July 8, 1976, now U.S. Pat. No. 4,038,977.

BACKGROUND OF THE INVENTION

This invention relates to an endoscope having a flexible sheath and in particular an endoscope equipped with a film cassette disposed within the forward end section of a sheath insertible into a body cavity of a human being and having a roll of film on which any affected portion of the body cavity can be photographed.

A conventional endoscope such as a gastroscope, includes a photographing device such as a patrone, cartridge or cassette (hereinafter referred to merely as a cassette) within the forward end portion of a sheath, and a body cavity of a human being is photographed through a photographing window provided at the forward end portion of the sheath. A film is sequentially fed frame by frame, during the photographing, into the sheath by a manual operation at a control section of the endoscope. Upon completion of photographing, the sheath is withdrawn from the body cavity of a human being and a cap member is removed from the forward end section of the sheath and an exposed film is taken out, together with the cassette, from the forward end section of the sheath. Therefore, there is a fear that the exposed film will be impaired due to the exposure of a daylight. It is required that the exposed film be taken out at a dark room.

Furthermore, since the exposed film is sequentially withdrawn from the cassette into the sheath, a restriction is imposed on the inner diameter or size of the sheath. That is, the inner diameter of the sheath can not be made too small due to the width of the film. In view of a current requirement that the inner dimension of a sheath be made minimal to alleviate pains of a patient, a problem is posed here. If the width of a film is made narrower instead of increasing the width of the sheath, an observed area corresponding to any affected portion of the inner cavity of a patient is narrowed, making it impossible for the observer to clearly and fully observe the affected portion of the inner cavity. As the width of the film is made narrower, there is a fear that the film will be torn apart. For this reason, the sheath can not be bent to a greater extent and in this sense a restriction is made to the flexibility of the sheath.

SUMMARY OF THE INVENTION

It is accordingly the object of this invention to provide an endoscope loaded with a cassette disposed within the forward end section of a sheath and having a roll of film, in which the film can be readily taken up in a simple arrangement.

In a preferred embodiment of this invention one end of a film take-up shaft externally extends from a cassette and a pully is fixed on the extending end of the film take-up shaft. A string has one end wound around the pully and the other end inserted through a single passage which is provided in the longitudinal direction of a flexible sheath. When the string is pulled by a manual operation at a control section of the endoscope, the pulley and thus the film take-up shaft are rotated as a unit to permit a film to be wound in an intermittent manner. In such arrangement, the single passage has only to be provided in the longitudinal direction of the sheath and the film per se is not passed through the single passage of the sheath. Therefore, a fine string can be used for a corresponding small diameter passage and in consequence it is not necessary that the outer diameter of the sheath be increased. Furthermore, the cassette can be taken out in broad daylight after a photograph is taken, and it is not necessary that an exposed film be taken out at a dark room.

In another embodiment of this invention, a rib means is provided in close proximity to an outer periphery of a pulley fixed on the end portion of a film take-up shaft which externally extends from a cassette. The rib means is cut out to a section from which a string is delivered. When the string is pulled for photographing, the rib means prevents the string from being disengaged from the pulley.

In a further embodiment, a loop of variable size is provided on the delivery end of a string and a hook provided on one end of an operating wire extending from a control section is releasably anchored to the loop of the string. When the string is pulled by the operating wire with the string anchored to the wire, the loop becomes smaller in size with the result that the loop is tied to the hook of the wire. When, therefore, the string is pulled through a single passage of a sheath, there is no fear that the loop will be disengaged from the hook. Furthermore, the string can be smoothly pulled with the loop tightened on the hook of the wire and in so doing the loop of the string undergoes no appreciable frictional contact with the inner wall of the small diameter single passage.

BRIEF DESCRIPTION OF THE DRAWING

FIG. 1 shows a general view, partially broken away, showing a film cassette equipped endoscope according to one embodiment of this invention;

FIG. 2 shows an enlarged longitudinal view as taken in a direction vertical to a film take-up shaft on the film cassette in FIG. 1;

FIG. 3 is a bottom view, partly broken away, showing the film cassette in FIG. 2;

FIG. 6 is a top view, partially broken away, showing the film cassette in FIG. 5;

FIG. 7 is an enlarged, cross-sectional view, as taken along line 7—7, showing the film cassette in FIG. 4; and FIG. 8 is a modified form of a connecting means between a string wound around a pulley on the film cassette and an operating wire provided within an endoscope body.

DESCRIPTION OF THE PREFERRED EMBODIMENT

Figure 4:
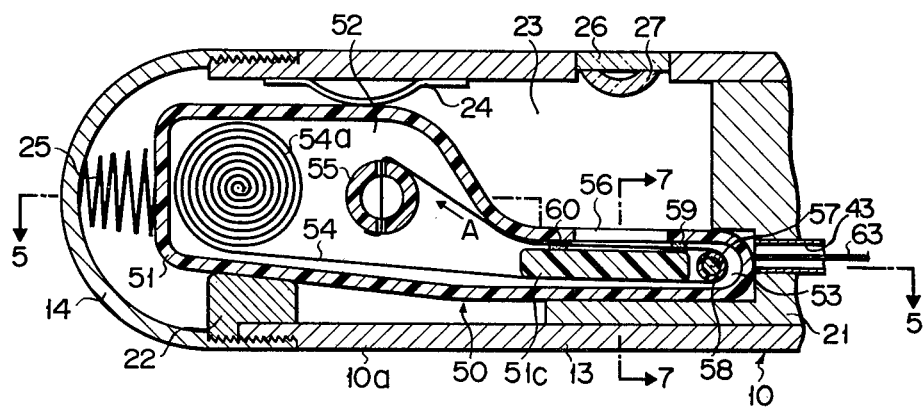
FIG. 4 is a partially enlarged view particularly showing only a forward portion of a film cassette equipped endoscope according to another embodiment of this invention.

FIG. 1 shows an endoscope according to this invention. The endoscope has a lengthy flexible sheath 10 and a control section 11 provided on the base end of the flexible sheath 10. The endoscope is, for example, a gastrofiberscope and the flexible sheath 10 is adapted to be inserted by the operation of the control section 11 into a body cavity (not shown) of a human being. The sheath 10 includes a flexible outer tube 12 extending substantially over the entire length thereof and only a forward end section 10a of the flexible sheath 10 comprises a cylindrical metal member 13 and a metallic cap member 14 threadably fitted over the free end of the member 13 and having a round outer surface. An image guide fiber bundle 15 and light guide fiber bundle 16 are disposed, in the longitudinal direction of the sheath 10, within the sheath 10 and optically connected to windows 17 and 18 in the cylindrical metal member 13. The bundle 15 sends an image corresponding to a body cavity (not shown) under observation of a human being to the control section 11 through the window 17 and the bundle 16 sends a light from the control section 11 through the window 18 to the body cavity under observation of the human being. The construction of the bundles 15 and 16 and their operation at the control section 11 is known in the art and further explanation is therefore omitted.

Within the forward end section 10a of the sheath 10 is disposed a film cassette or cartridge 20 (hereinafter referred to merely as a cassette) loaded with a rolled film 19. The cassette 20 is positioned, by cassette positioning frame members 21 and 22, within a cassette chamber 23 in the forward end section 10a of the sheath 10 and securely held by a leaf spring 24 and coil spring 25 in a set position. The positioning frame members 21 is fixed to the inner surface of the member 13 and the positioning frame member 22 is fixed to the front end surface of the member 13. The leaf spring 24 has one end fixed to the inner surface of the member 13 and the coil spring 25 has one end fixed to the inner surface of the cap member 14. A photographing window 26 is provided in the cylindrical metal member 13 and a photographing lens 27 is disposed in proximity to the photographing window 26.

As shown in full in FIGS. 2 and 3 the cassette 20 has a housing means 30 comprising a pair of side housings 30a, 30b and a main housing 30c. With the cassette 20 in a state shown in FIG. 1 an exposure window 31 optically connected to the optical system 26, 27 is opened in the housing means 30 and thus the main housing 30c. A roll shaft 33 is disposed in a film roll chamber 32 which is located at one side of the housing means 30 (to the left of the cassette 20 in FIG. 2), and a film 19 is rolled around the roll shaft 33 to provide a film roll body 19a. A film take-up shaft 35 is disposed in a chamber 34 which is located at the other side (to the right of the cassette 20) of the housing means 30 with an exposure window 31 between the chambers 32 and 34. The film 19 is supplied in a direction indicated by an arrow A in FIG. 2, i.e., from the roll shaft 33 through an exposure window 31 to the take-up shaft 35 in the chamber 34 in the cassette 20. The shafts 33 and 35 are rotatably supported on the side housings 30a and 30b. Light shielding filters 36 and 37 prevent an entry into the chambers 32 and 34 of a light which is incident from the exposure window 31 into the cassette 20. The film 19 is sent through the light shielding filters 36 and 37.

As shown in FIG. 3 one end of the take-up shaft 35 has a shaft means 40 integral therewith. The shaft means 40 outwardly extends from the side housing 30a and a pulley 41 is fixed to the shaft means 40. Unlike this embodiment, the shaft means 40 is formed separately from the take-up shaft 35 and it can be rotated as a unit with the take-up shaft 35. The pulley 41 may be formed integral with the shaft means 40.

One end of a string 42 is wound around a pulley 41 and the string 42 is made of a suitable flexible material free from expansion and contraction. The end portion of the string 42 is doubled back upon itself with the free end thereof fixed as at 42b to provide a loop 42a. In consequence, the loop has a predetermined size. When the string 42 is pulled in a direction indicated by B in FIG. 3, the take-up shaft 35 is rotated through the pulley 41 and shaft means 40 to permit the film 19 to be taken up in a direction of A in FIG. 2.

As shown in FIG. 1 a single passage 43 with a small inner diameter of about 1 mm is provided in the sheath 10 along the longitudinal direction of the sheath 10. For example, the passage 43 is provided by a slender tube. The passage 43 extends from the frame 21 to the control section 11 and the string 42 is passed through the passage 43 as shown in FIG. 1.

A spring pulling means, i.e., an operating wire 44 is provided in the endoscope and the string 42 can be pulled away from the shaft 35 by operating the wire 44 at the control section 11. The operating wire 44 has a hook 44a at the forward end and the hook 44a is removably anchored to the loop 42a of the string 42. The wire 44 is made of a suitable, relatively pliable material free from expansion and contraction. The base end of the wire 44 is fixed to a take-up drum 45 in the control section 11 and the drum 45 is connected to a rotation operating knob 46 which projects outside of the control section 11. When the knob 46 is rotated, the wire 44 is taken up on the drum 45. It will be understood that, when the knob 46 is rotated in one direction, the film 19 in the cassette 20 is sequentially taken up in a direction indicated by the arrow A in FIG. 2.

When an intended photographing is completed through the cassette film 19, the sheath 10 is withdrawn from the body cavity of the human being and the cap member 14 is unscrewed and the cassette 20 is removed from the cassette chamber 23. In this case, the string 42 and operating wire 44 are drawn out together. It will be sufficient if the wire 44 is drawn out to a position where the hook 44a anchored to the string 42 appears outside. The hook 44a of the wire 44 is removed from the loop 42a of the string 42 and the string 42 is again suitably wound on the pulley 41. The rolled film 19 can be taken out from the film cassette 20 by removing the side housing 30b from the main housing 30c.

FIGS. 4 to 7 shows an endoscope according to a second embodiment of this invention. In this embodiment the structure of a sheath and control section is substantially similar to that of the first embodiment except for the interior arrangement of a forward end section of a sheath, and therefore only a different part of the sheath is shown in these Figures. The second embodiment is different from the first embodiment in the structure per se of a film cassette. Like reference numerals are employed to designate like parts or elements corresponding to those shown in the first embodiment, with an addition of different reference numerals to different parts or elements.

In FIG. 4 a film cassette 50 is received in a cassette chamber 23 in the forward end section 10a of a flexible sheath 10. A means for positioning the film cassette 50 within the cassette chamber 23, that is, frame members 21 and 22, leaf spring 24 and coil spring 25 is substantially similar to that of the first embodiment, but the shape of the frame members 21 and 22 and the mounting of the leaf spring 24 on a cylindrical metal member 13 are somewhat different from those of the first embodiment.

Figure 5:
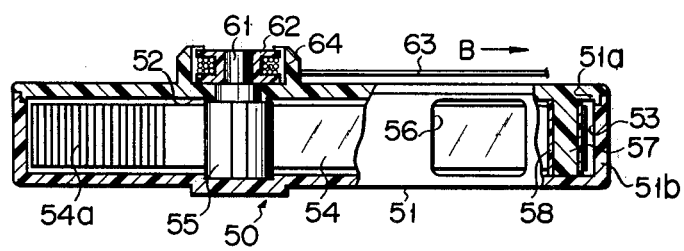
FIG. 5 is a partially cross-sectional view, as taken along line 5—5, showing the film cassette in FIG. 4.

A cassette 50 has a housing means 51 consisting of two side housings 51a and 51b removably fitted one on the other. An enlarged chamber 52 is provided at one side of the housing means 51 (to the left in FIG. 4) and a flattened chamber 53 is provided at the other side of the housing means 51 (to the right in FIG. 4). A film roll body 54a of a rolled film 54 and a film take-up shaft 55 are disposed in the enlarged chamber 52 and the film take-up shaft 55 is rotatably supported on the side housings 51a and 51b. An exposure window 56 is formed on the side housing 51b of the housing means 51. As shown in FIG. 7 a partition section 51c is integrally projected from the side housing 51a and fitted into the housing 51b and as shown in FIG. 5 a film guide shaft 57 is integrally projected from the housing 51a. A collar 58 is fitted over the film guide shaft 57. It will be understood that the film guide shaft 57 can be formed independently of the housing 51a.

The film 54 is delivered from the film roll body 54a, down through the partition section 51c, to the film guide shaft 57 where it is U-turned and fed in a direction of an arrow A in FIG. 4 toward a take-up shaft 55. That is, the U-turned film is fed up through the partition section 51c, while passing through an exposure window 56, to the take-up shaft 55. Unlike the first embodiment, no support shaft is provided for the film roll body 54a. Even in the absence of such support shaft no inconvenience is involved in the film delivery. Light shielding filters 59 and 60 perform the same function as those shown in the first embodiment.

With a cassette 50 equipped in a cassette chamber 23 the exposure window 56 of the cassette 50 is optically connected to an optical system, i.e., a photographing window 26 and photographing lens 27.

As shown in FIGS. 5 and 6 one end of the take-up shaft 55 externally extends from the side housing 51a to provide a shaft means 61 on which a pulley 62 is mounted. A string 63 is wound around the pulley 63. When the string 63 is delivered in a direction of an arrow B, the take-up shaft 55 is rotated through the pulley 62 and thus the shaft means 61. In this way, the film 54 is taken up as in the first embodiment. In close proximity to the outer periphery of the pulley 62 an annular rib 64 is provided integral with the side housing 51a. The annular rib 64 is formed concentric with the rotation axis of the pulley 62. The annular rib 64 is partially cut to leave an arcuate section, and the cut-out section 65 of the rib 64 permits the string 63 to be delivered therefrom. The presence of the rib 64 prevents the string 63 from being unwarrantedly disengaged from the pulley 62. The rib 64 can be formed separately from the housing 51a and in this case it is fitted on the housing 51a. The cassette 50 in the second embodiment has the following advantages. The length of the cassette 50 can be shortened, since the film roll body 54a and take-up shaft 55 are disposed in the enlarged chamber 52. To explain more in detail, a distance between the film roll body 54a and the take-up shaft 55 can be minimized, since the diameter of the film roll body 54a is decreased with a delivery of the film 54 from the film roll body 54a and since the diameter of a roll of film wound around the take-up shaft 55 is correspondingly increased. As mentioned above, the extent to which the string 63 is unwarrantedly disengaged from the pulley 62 can be reduced to a minimum. This avoids any inconvenience when the sheath is inserted into the body cavity of a patient and a photograph is taken during the observation of the body cavity.

FIG. 8 is a modified form of an anchoring means between a string and an operating wire. In this Figure, a string 71 is wound around a pulley 70 as in the case of the first and second embodiments and it corresponds to the strings 42 and 63 in the first and second embodiments, respectively. An operating wire 72 in this embodiment corresponds to the operating wire 44 shown in the first embodiment. A loop 71a is formed, as a delivery end, in the free end portion of the string 71 and a small loop 71b is also formed at the fixed portion of the loop 71a so that, when the small loop 71b is slidably moved along the string 71, the size of the loop 71a can be varied. A grip portion 71c extends from a knot of the small loop 71b. A hook 72a is formed, as in the first embodiment, at the free end portion of a wire 72. The hook 72a of the wire 72 is anchored to the variable loop 71a.

Such anchoring means has the following advantages. When the wire 72 is pulled in a direction of an arrow B, the size of the loop 71a becomes smaller and smaller, since the small loop 71b is slidably moved toward the hook 72a of the wire 72. As a result, the hook 72a and the loop 71a are closely tied together.

The single passage of the sheath has a small diameter of about 1 mm and the loop of the string and hook of the operating wire is correspondingly small in size and there is a fear that the hook will be disengaged from the loop of the string. Since according to this invention the size of the loop can be varied, the loop is positively tied to the hook during the pulley operation. When the loop 71a is desired to be released from the hook 72a, the grip portion 71c of the string 71 is pulled away from the hook 72a and it will be easily released from the hook 72a, since the size of the loop 71a become larger. Furthermore, the string can be pulled with a minimum frictional contact with the inner wall surface of the passage of the sheath, since the loop 71a of string 71 is compactly tied on the hook 72a of the wire 72.

What is claimed is:

1. A film cassette for an endoscope comprising a cassette housing means with an exposure window and with a film received therein, a film take-up shaft rotatably supported by said cassette housing means, and a string frictionally engaging said film take-up shaft so as to wind up said film when said string is pulled, said film take-up shaft including a pulley around which one end portion of said string is wound, said cassette housing means being provided with a rib close to the outer periphery of said pulley and having at least one cut-out section from which said string is delivered, the remaining portion of said rib preventing said string from being disengaged from said pulley.

2. The film cassette according to claim 1, in which said rib is integral with said cassette housing means.

* * * * *